US008193248B2

(12) United States Patent
McCarthy

(10) Patent No.: US 8,193,248 B2
(45) Date of Patent: Jun. 5, 2012

(54) CONTRACEPTIVE COMPOSITION

(75) Inventor: Thomas David McCarthy, Malvern East (AU)

(73) Assignee: Starpharma Pty Limited, Melbourne, Victoria (AU)

( * ) Notice: Subject to any disclaimer, the term of this patent is extended or adjusted under 35 U.S.C. 154(b) by 790 days.

(21) Appl. No.: 12/294,024

(22) PCT Filed: Mar. 21, 2007

(86) PCT No.: PCT/AU2007/000352
§ 371 (c)(1),
(2), (4) Date: Oct. 16, 2008

(87) PCT Pub. No.: WO2007/106944
PCT Pub. Date: Sep. 27, 2007

(65) Prior Publication Data
US 2009/0275507 A1 Nov. 5, 2009

(30) Foreign Application Priority Data

Mar. 22, 2006 (AU) ................................ 2006901474

(51) Int. Cl.
*A01N 37/18* (2006.01)
*A61K 31/16* (2006.01)
(52) U.S. Cl. ........................................ 514/616; 977/754
(58) Field of Classification Search .................. 514/616; 977/754
See application file for complete search history.

(56) References Cited

U.S. PATENT DOCUMENTS

| 5,229,490 A | 7/1993 | Tam | |
|---|---|---|---|
| 2002/0015697 A1* | 2/2002 | Beckman et al. | 424/94.4 |
| 2004/0094163 A1* | 5/2004 | Benson | 128/844 |

FOREIGN PATENT DOCUMENTS

| JP | 9512264 A | 12/1997 |
|---|---|---|
| JP | 2004515457 A | 5/2004 |
| JP | 2005532276 A | 10/2005 |
| WO | 95/28966 A1 | 11/1995 |
| WO | WO 95/34595 A1 | 12/1995 |
| WO | WO 98/03573 A1 | 1/1998 |
| WO | WO 00/15239 A1 | 3/2000 |
| WO | WO 00/15240 A1 | 3/2000 |
| WO | 01/87348 A2 | 11/2001 |
| WO | WO 02/079299 * | 10/2002 |
| WO | WO 02/079299 A1 | 10/2002 |
| WO | 03/076455 A2 | 9/2003 |

OTHER PUBLICATIONS

Glasier (Expert Opinion on Investigational Drugs (2002) 11:1239-1251).*
J. G. Cannon, Chapter Nineteen in Burger's Medicinal Chemistry and Drug Discovery, Fifth Edition, vol. I: Principles and Practice, Wiley-Interscience 1995, pp. 783-802).*
Lewis, "Track A: Basic Science, AP12-202 Contraceptive Properties of Vivagel", Starpharma Pty Ltd, Australia, Feb. 24-27, 2008.
Tyssen, et al., "Structure Activity Relationship of Dendrimer Microbicides with Dual Action Antiviral Activity", Plos One, vol. 5, Issue 8, Aug. 2010.
Telwatte, et al., "Virucidal activity of the dendrimer microbicide SPL7013 against HIV-1", Antivral Research, Apr. 7, 2011.
Liu, et al., Water Soluble Dendrimer-Poly(ethylene glycol) Starlike Conjugates as Potential Drug Carriers, Journal of Polymer Science Part A: Polymer Chemistry, vol. 37, Mar. 25, 1999, pp. 3492-3503.

* cited by examiner

*Primary Examiner* — Marcos Sznaidman
(74) *Attorney, Agent, or Firm* — Knobbe, Martens, Olson & Bear, LLP

(57) ABSTRACT

The present invention relates to a contraceptive composition including an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefor. The contraceptive composition may also exhibit antimicrobial activity. The invention also relates to a method of selectively reducing or preventing conception in a female animal, including a human, which method includes administering to the animal an effective amount of a contraceptive composition which composition includes an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefor.

17 Claims, No Drawings

CONTRACEPTIVE COMPOSITION

The invention was made with United States Government support under U19 AI060598 awarded by the National Institutes of Health (NIH). The Government has certain rights in the invention.

This application is U.S. National Phase of International Application PCT/AU2007/000352, filed Mar. 21, 2007 designating the U.S., and published in English as WO 2007/106944 on Sept. 27, 2007, which claims priority to Australian Patent Application 2006901474, filed Mar. 22, 2006.

FIELD OF THE INVENTION

The present invention relates to a pharmaceutical composition and method of preventing pregnancy and, in particular, to the use of dendrimer compounds including naphthyl disulphonic acid surface groups.

BACKGROUND OF THE INVENTION

Spermicides are one of a number of contraceptive methods known in the prior art. The most popular spermicide contains Nonoxynol-9 (N9) as the active ingredient. However, N9 does not provide the user with protection against sexually transmitted infections (STIs), such as Human Immunodeficiency Virus (HIV), Herpes simplex virus (HSV) and other viral and microbial pathogens. In fact, N9, which is a detergent based spermicide, may actually have adverse effects in the prevention of STIs. Whilst such detergents act to disrupt HIV and HSV membranes, they may also compromise the natural vaginal barrier and significantly increase susceptibility to infection.

International patent application no PCT/AU02/00407 (WO 02/079299), to applicants, the entire contents of which are incorporated herein by reference, discloses a class of dendrimers (highly branched macromolecules with a defined envelope of polyanionic or cationic surface groups) which have been shown to exhibit a range of antiviral and antimicrobial activity with minimal toxicity.

For example, polylysine, polyamidoamine (PAMAM), poly(etherhydroxylamine) (PEHAM) and polypropyleneimine dendrimers including the compounds represented by Formulae I to III below and bearing naphthyl disulphonic acid surface groups, have been shown to exhibit antimicrobial activity, particularly antiviral activity.

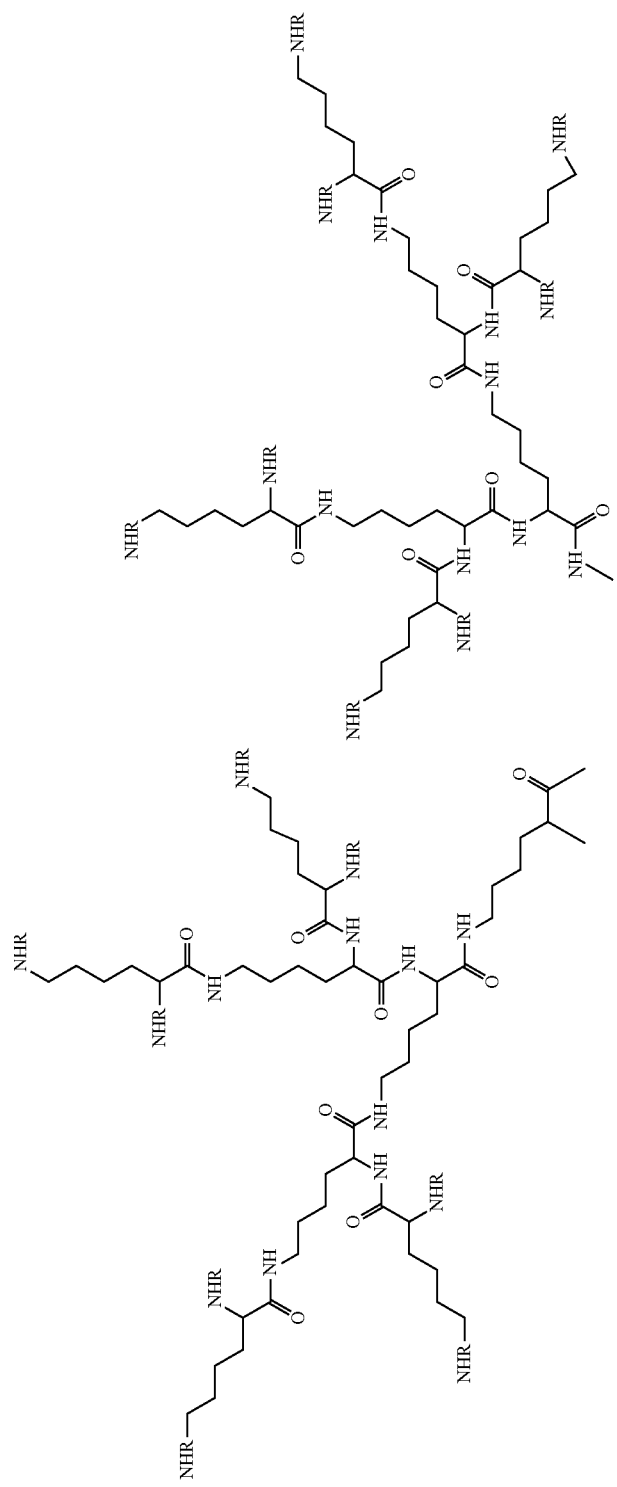

-continued
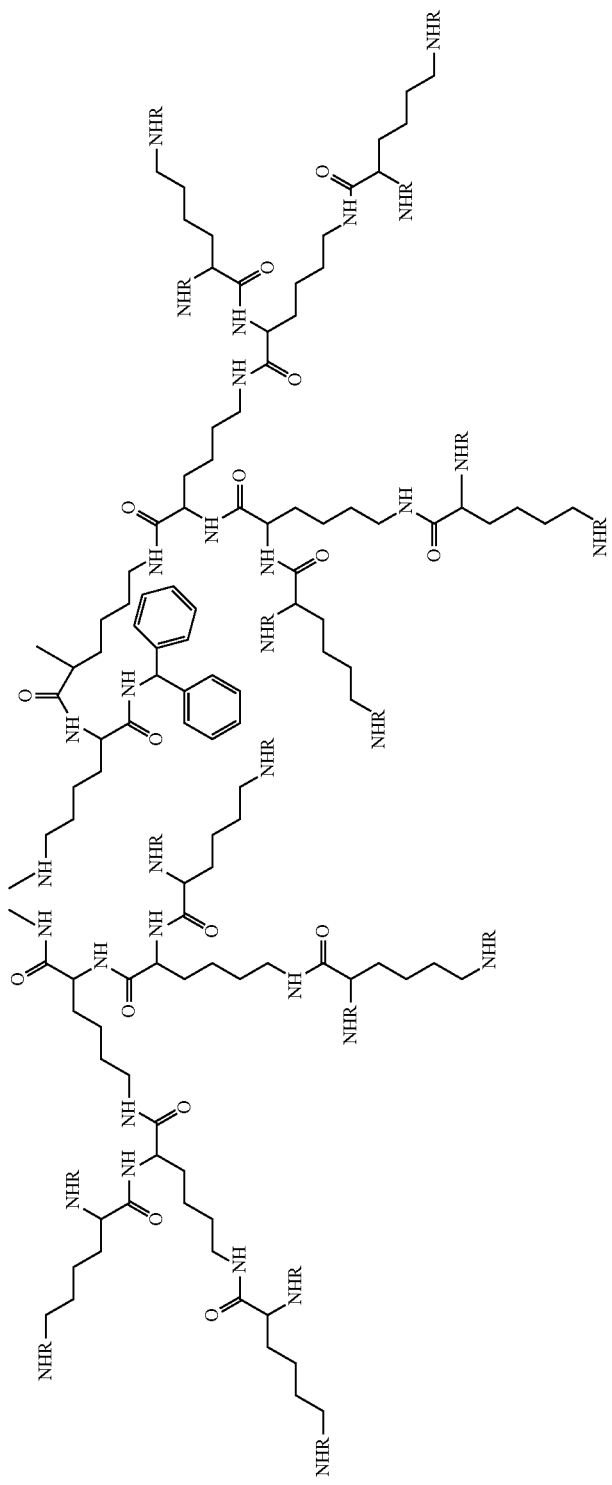

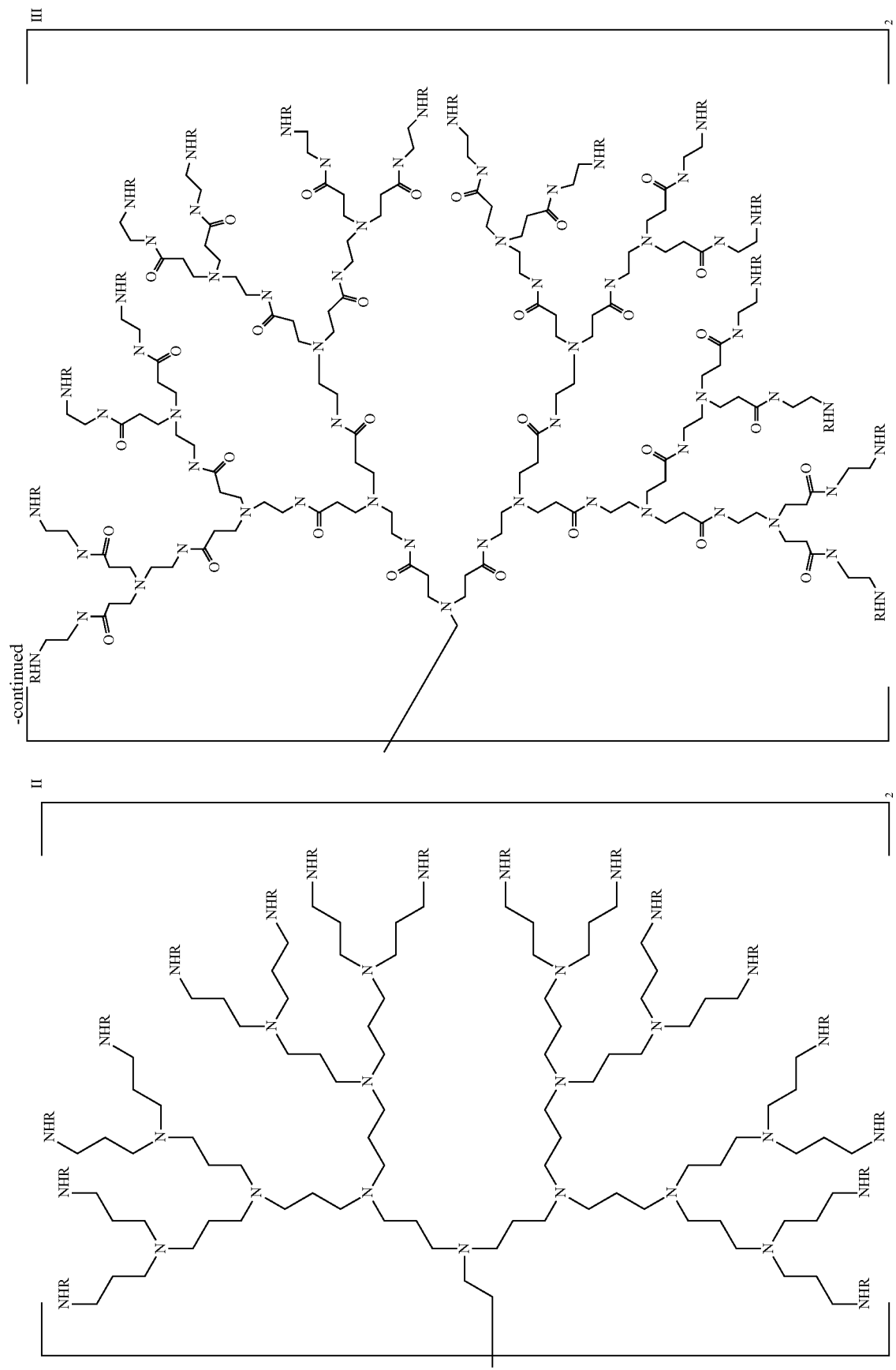

where R represents a group of the Formula IV:

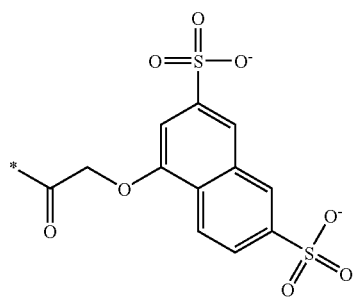

IV

It would accordingly be a significant advance in the art if a contraceptive compound could be provided as an alternative to the spermicides including N9 currently known in the art, which does not have adverse effects in the prevention or transmission of STIs.

SUMMARY OF THE INVENTION

The Applicants have surprisingly discovered that certain dendrimer compounds with naphthyl disulphonic acid surface groups, as well as exhibiting antimicrobial activity, may also function as contraceptives.

In a first aspect of the present invention there is provided a contraceptive composition including
  an effective amount of a dendrimer compound including one or more naphthyl disulphonic acid surface groups, or a pharmaceutically acceptable salt or solvate of the dendrimer compound; and
  a pharmaceutically acceptable carrier, excipient and/or diluent therefor.

The contraceptive composition may be provided in a topical form, such as a foam, gel, cream, film, or the like. The composition may be administered at any time during sexual intercourse, but preferably before and during sexual intercourse.

In a further embodiment, the contraceptive composition may further include a secondary pharmaceutically active component.

In a preferred embodiment, the contraceptive composition may also exhibit antimicrobial activity. Preferably the antimicrobial activity is towards sexually transmitted infections (STIs). Preferably the antimicrobial activity is antiviral activity toward viral sexually transmitted infections (STIs) including HIV, HSV, Hepatitis B and C (HBV and HCV), Human Papilloma Virus (HPV) and Cytomegalovirus (CMV).

In another aspect of the invention there is provided a method of selectively reducing or preventing conception in a female animal. The method includes administering to the animal an effective amount of a contraceptive composition, which composition includes
  an effective amount of a dendrimer compound including one or more naphthyl disulphonic acid surface groups, or a pharmaceutically acceptable salt or solvate of the dendrimer compound; and
  a pharmaceutically acceptable carrier, excipient and/or diluent therefor.

The composition included in the method may further include a secondary pharmaceutically active component.

In yet another aspect the contraceptive composition may be carried on a surface of a prophylactic device with which it is compatible.

DETAILED DESCRIPTION OF THE EMBODIMENTS

As used herein in this specification and claims, the singular forms "a", "an" and "the" include plural referents unless the context clearly dictates otherwise.

The term "comprises" (or its grammatical variants) as used herein in this specification and claims is equivalent to the term "includes" and should not be taken as excluding the presence of other elements or features.

Compositions containing certain dendrimer compounds with napthyl disulphonic acid surface groups have unexpectedly exhibited contraceptive activity. By the term "contraceptive activity" as used herein in this specification and claims we mean activity that prevents or reduces the likelihood of a female animal becoming pregnant or giving birth.

The contraceptive activity of a composition in general may be conferred by a number of mechanisms.

N9 for example is spermicidal, killing sperm to prevent them from fertilising an ova. Non-spermicidal contraceptive compositions may function to change the environment in the vagina. For example a hypertonic composition may result in hardening of the cervical mucus, thereby preventing or hindering entry of sperm into the cervix. Other compositions may form a matrix when they come in contact with ejaculate in the vagina, which traps the sperm and again limits their ability to reach the cervix. Maintaining the acidic environment with the vagina can also assist in inactivating sperm, particularly after ejaculation when the vagina pH increases from about 4 to a more "sperm friendly" neutral to slightly basic environment.

Alternatively, a contraceptive composition may induce acrosomal loss. Acrosomes contain enzymes that allow penetration of the sperm into the ova. Similarly, the enzyme hyaluronidase is required to disperse follicular cells surrounding the ova, thereby permitting sperm penetration. As such, compositions that can inhibit this enzyme may have contraceptive activity.

The same contraceptive compositions of the invention additionally exhibited antimicrobial activity. By the term "antimicrobial activity" as used herein in this specification and claims we mean a composition, or components thereof, that kills or inhibits the growth of microbes such as bacteria, viruses, fungi and parasites.

By the term "dendrimer compound" as used herein in this specification and claims we mean any suitable highly branched macromolecules. The dendrimer compound may be of any suitable type. Preferably the dendrimer compound includes a polylysine, polyamidoamine (PAMAM), poly (etherhydroxylamine) (PEHAM) or polypropyleneimine dendrimer scaffold. More preferably, the dendrimer compound is selected from a compound of Formula I, II or III:

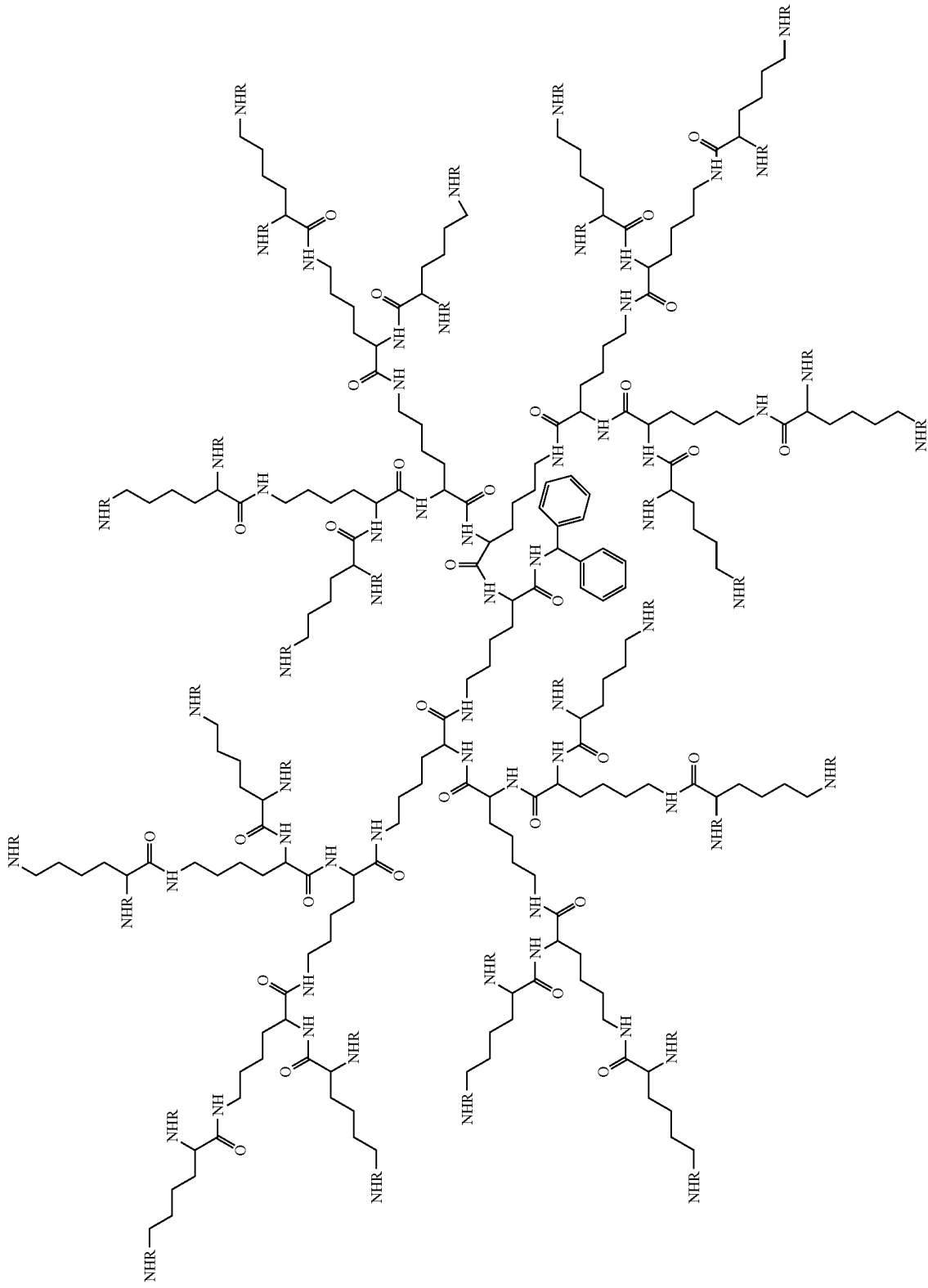

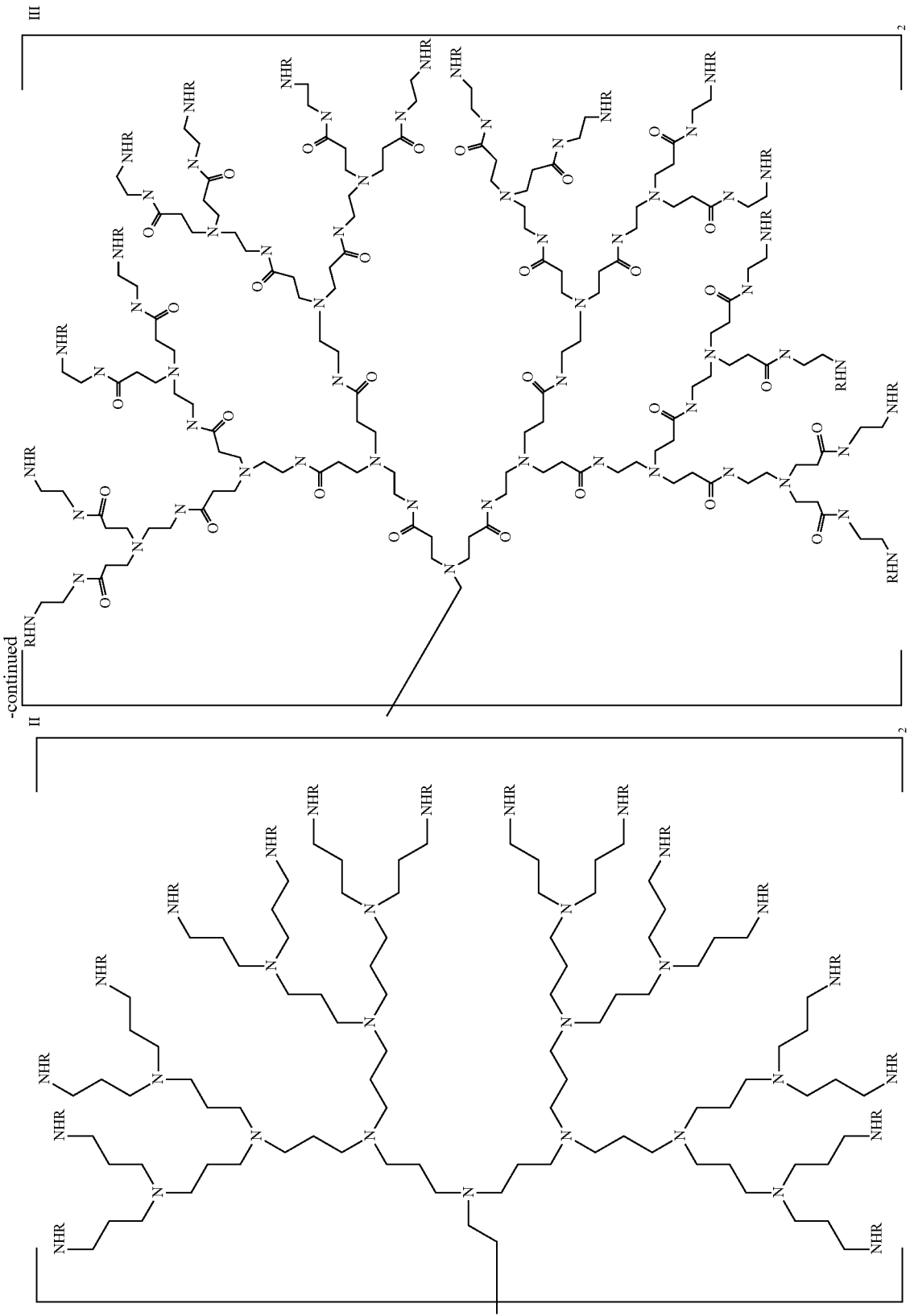

where R represents a group of Formula IV:

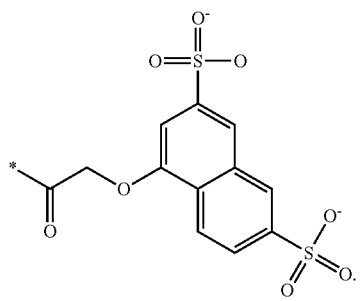

Accordingly, in a first aspect of the present invention, there is provided an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefor. The dendrimer compound of Formula I is particularly preferred.

The dendrimer compound may be present in the contraceptive composition in any suitable amount. Preferably, the dendrimer compound is present in the composition in an amount of from approximately 0.5% to 70% by weight, based on the total weight of the composition. More preferably, the dendrimer compound is present in an amount of from 1% to 50% by weight, most preferably 1% to 30% by weight, based on the total weight of the composition.

Suitable pharmaceutically acceptable base addition salts include, but are not limited to, metallic salts such as the aluminium, calcium, lithium, magnesium, potassium, sodium and zinc salts, as well as organic salts made from organic amines such as N,N"-dibenzylethlenediamine, chloroprocaine, diethanolamine, ethylenediamine, dicyclohexylamine, meglumine (N-methylglucamine) and procaine, quaternary amines such as choline and sulphonium and phosphonium salts.

The contraceptive composition may be a topical composition, preferably provided in the form of a foam, gel, cream, film or the like. Suitable pharmaceutically acceptable carriers, excipients and diluents may include one or more of any and all conventional solvents, dispersion media, fillers, solid carriers, aqueous solutions, coatings, vehicles suitable for topical administration, other antimicrobial agents, isotonic and absorption enhancing or delaying agents, activity enhancing or delaying agents for pharmaceutically active substances, and are well known in the art. They are described, by way of example, in *Remington's Pharmaceutical Sciences*, 18th Edition, Mack Publishing Company, Pennsylvania, USA. Except insofar as any conventional carrier, excipient or diluent incompatible with the active agent, use thereof in the contraceptive composition of the present invention is contemplated.

Vehicles suitable for topical administration include oil-in-water and water-in-oil emulsions, white petrolatum, hydrophilic petrolatum, lanolin emulsions, polyethylene glycols, cocoa butter, mucoadhesives, gelling agents, buffering agents, emollient oils (e.g. water-soluble oils including, for example, polyethylene glycol), a lubricating gel (including, for example, water, propylene glycol, hydroxyethyl cellulose, benzoic acid and sodium hydroxide), a water-soluble oil (including, for example, glycerine, propylene glycol, polyquaternium #5, methyl paraben and propyl paraben), a cream (including, for example, benzyl alcohol, cetearyl alcohol, cetyl esters, wax, octyldodecanol, polysorbate 60, purified water, and sorbitan monostearate), and the like.

Preferably, the carriers, excipients and/or diluents include one or more of the group consisting of sodium hydroxide, water soluble oils, mucoadhesives, gelling agents, buffering agents, lubricating gels, propylene glycol, glycerine and water.

More preferably, the carriers, excipients and/or diluents include one or more of the group consisting of sodium hydroxide, water soluble oils, Carbopol®, propylene glycol, glycerine, hydroxyethylcellulose and water. More preferably, they include sodium hydroxide, EDTA disodium dihydrate, methyl paraben, propyl paraben, Carbopol® 971P, propylene glycol, glycerine, and purified water in combination.

In a preferred embodiment, the contraceptive composition may also exhibit antimicrobial activity. Preferably the antimicrobial activity is towards microbes that cause sexually transmitted infections (STIs). The contraceptive composition according to the present invention may be administered in an amount sufficient for the prevention of sexually transmitted infections. This amount may depend on the particular sexually transmitted infection sought to be prevented, and individual patient parameters including age, physical condition, size, weight and concurrent treatment(s). These factors are well known to those of ordinary skilled in the art and can be addressed with no more than routine experimentation.

Common causes of STIs include, but are not limited to papillomaviruses, Chlamydia trachomatis, Candida Albicans, Trichomonas vaginalis, Herpes simplex viruses (HSV), Cytomegalovirus (CMV), Neisseria gonorrhoeae, Human Immunodeficiency virus (HIV), Treponema pallidum, Hepatitis B and C viruses (HBV and HCV), Calymmato bacterium granulomatis, Haemophilus ducreyi, Sarcoptes scabeie, Phthirus pubis, Mycoplasma, Gardnerella vaginalis.

Preferably the antimicrobial activity is antiviral, exhibiting activity against sexually transmitted viruses including HIV, HSV, HCV, HBV, human papillomavirus (HPV) and CMV.

The contraceptive composition of the present invention may further include a secondary pharmaceutically active component exemplified by, but not limited to, one or more compounds selected from the group consisting of:

| | | |
|---|---|---|
| Anaesthetics | Analgesics | Anti-parasitic agents |
| Antibacterials | Antibodies | Antivirals |
| Anti-fungals | Anti-inflammatories | Anti-protozoals |
| Anti-infectives | Anti-microbials | Biologicals |
| Contraceptives | Hormones and analogs | Minerals |

| | -continued | |
|---|---|---|
| Muscle relaxants | Natural products | Nutraceuticals and nutritionals |
| Pain therapeutics | Peptides and polypeptides | Vitamins |

Preferably, the secondary pharmaceutically active component is selected from one or more of the group consisting of secondary microbicidal components, spermicides and contraceptive agents. The secondary pharmaceutically active component may be selected from one or more of the group consisting of, but not limited to, podophyllin, tetracycline, nystatin, fluconazole, metronidazole, acyclovir, penicillin, cefotaxime, specinomycin, retrovir, erythromycin, ceftriaxone, cotrimoxazole, cotrimoxazole, benzyl benzoate, malathion, menfegol, progestin, estrogen, estradiol, and the like. Other suitable secondary pharmaceutically active components suitable for preventing contraception and preferably preventing STIs would be known to the skilled person.

There is also provided a contraceptive antimicrobial composition including an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefore.

Such a composition may be used to selectively reduce or prevent conception, and prevent sexually transmitted infections particularly viral sexually transmitted infections.

In a further aspect of the present invention, there is provided a method of selectively reducing or preventing conception in a female animal, including a human, which method includes administering to the animal an effective amount of a contraceptive composition which composition includes an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefor.

The contraceptive composition may be administered at any time, ie, before and/or during and/or after sexual intercourse, but preferably before and/or during sexual intercourse.

The contraceptive composition included in the method of the present invention may further include a secondary pharmaceutically active component as described above.

The dendrimer compounds described above may also be used for the manufacture of a medicament for selectively reducing or preventing conception in a female animal.

Preferably, the dendrimer compounds include a polylysine, polyamidoamine (PAMAM), poly(etherhydroxylamine) (PEHAM) or polypropyleneimine dendrimer scaffold. More preferably, the dendrimer compound is selected from a compound of Formula I, II or III:

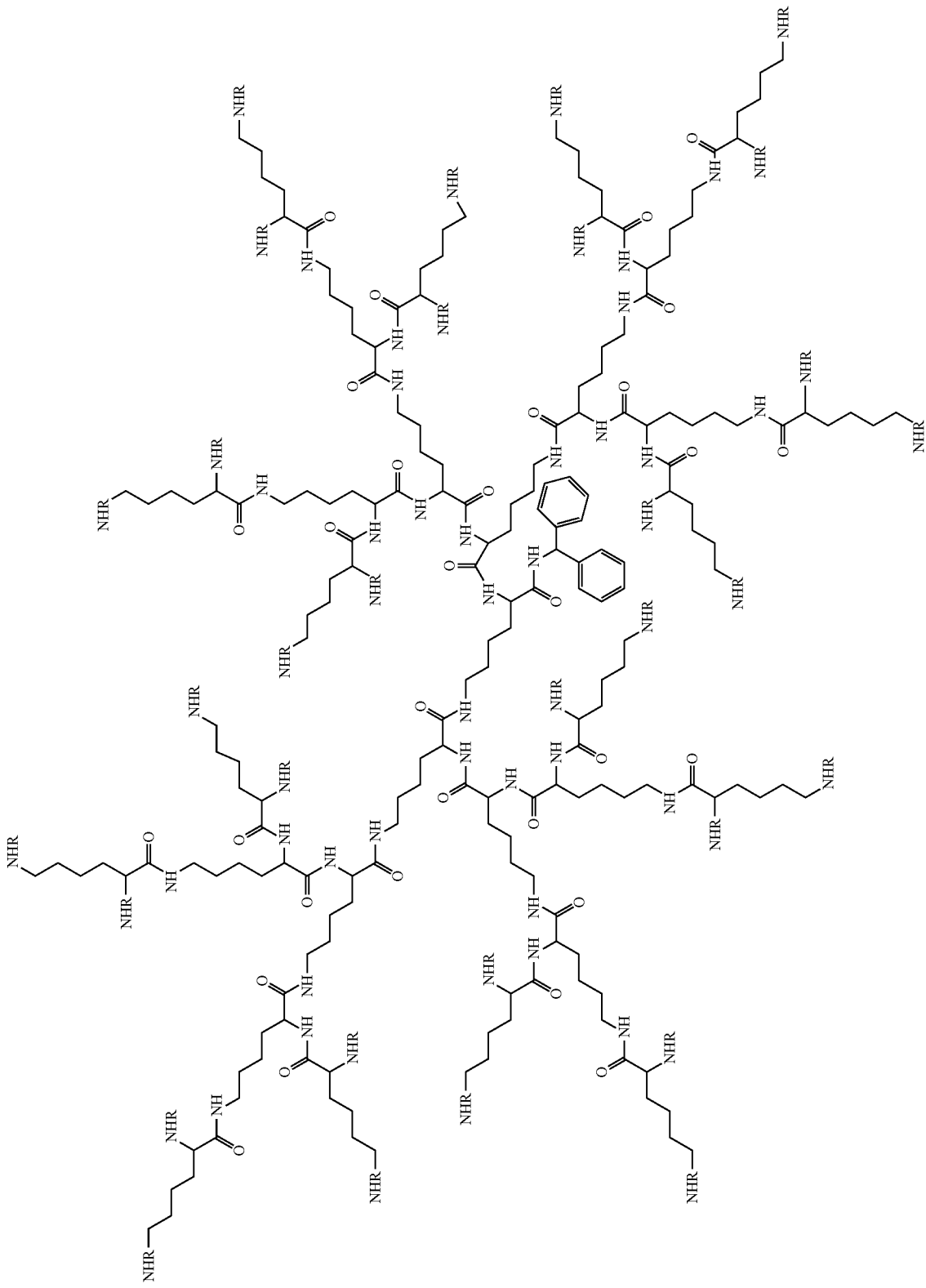

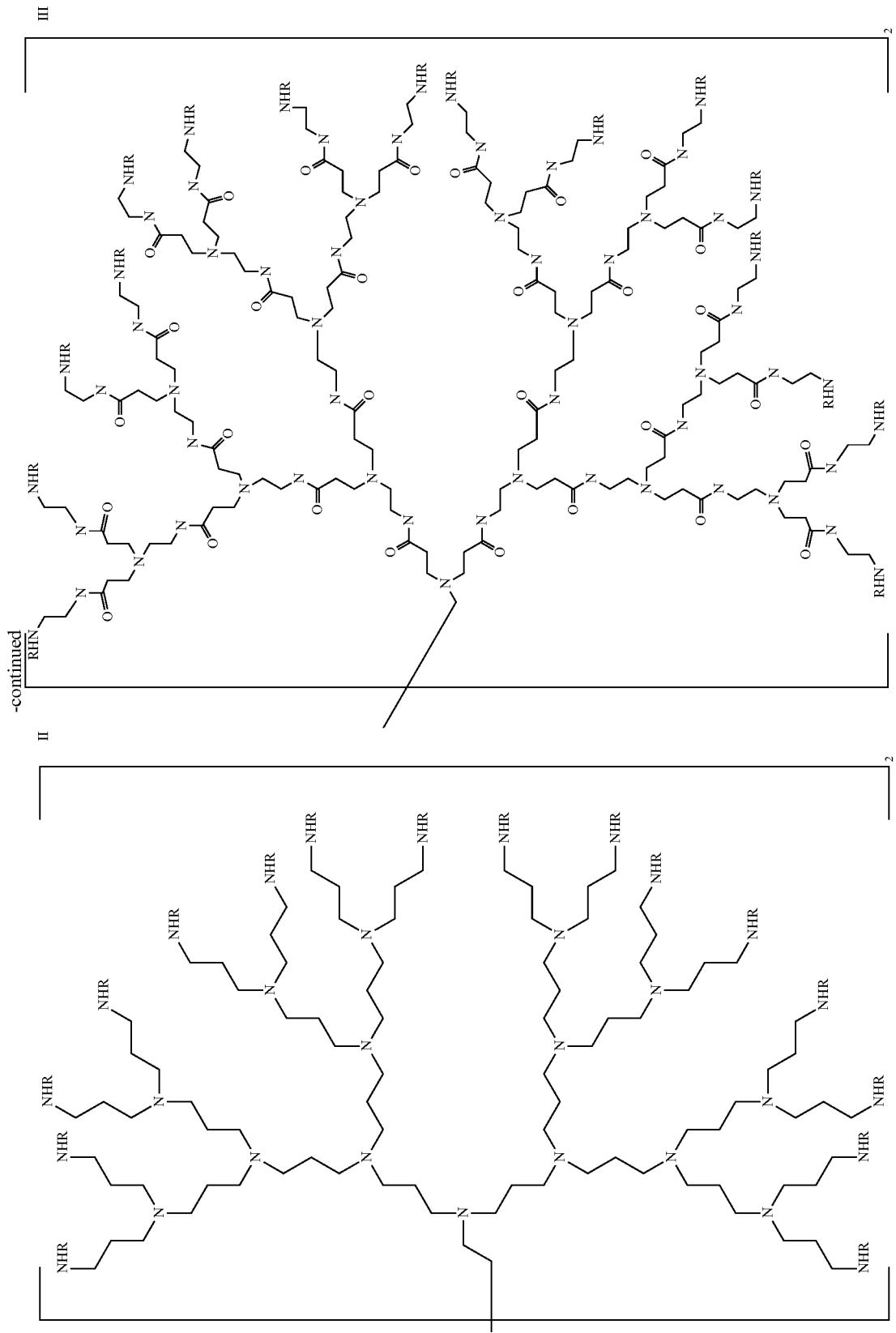

where R represents a group of Formula IV:

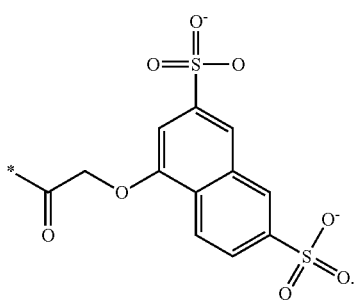

The dendrimer polymer of formula I is particularly preferred.

In yet another aspect of the invention, there is provided a method of selectively reducing or preventing conception in a female animal, including a human, and preventing one or more sexually transmitted infections. The method includes administering to the animal an effective amount of a contraceptive composition which composition includes an effective amount of a dendrimer compound including one or more naphthyl disulphonic acid surface groups, or a pharmaceutically acceptable salt or solvate of the dendrimer compound; and a pharmaceutically acceptable carrier, excipient and/or diluent therefor.

Preferably the STIs that are prevented are viral STIs, including HIV, HSV, HBV, HCV, HPV and CMV infections.

The dendrimer compounds described above may also be used for the manufacture of a medicament for selectively reducing or preventing conception in a female animal, and preventing one or more sexually transmitted infections.

In a still further aspect of the present invention the contraceptive composition may be carried on a surface of a prophylactic device with which it is compatible. Accordingly, there is provided a method of selectively reducing or preventing conception in a female animal, including a human, which method includes providing:

an effective amount of a contraceptive composition including
a dendrimer compound including one or more naphthyl sulphonic acid surface groups, or a pharmaceutically acceptable salt or solvate of the dendrimer compound; and
a pharmaceutically acceptable carrier, excipient and/or diluent therefor; and
a prophylactic device;
the contraceptive composition being carried on a surface of the prophylactic device and being compatible therewith.

The prophylactic device may be of any suitable type. A condom, cervical cap, contraceptive diaphragm, vaginal sponge, intrauterine device, pessary or the like may be used. A condom is preferred.

The dendrimer compound may contact a surface of the prophylactic device in any suitable manner. For example, the dendrimer compound may be coated on, or impregnated into, one or more surfaces of the prophylactic device. The dendrimer compound may be covalently bound to one or more surfaces of the prophylactic device.

The dendrimer compound according to the method of the present invention may be administered in an amount sufficient to prevent pregnancy.

For example, the amount of dendrimer compound included in the contraceptive composition of the present invention may be in the range of 0.5 to 70% by weight based on the total weight of the composition.

The amount of contraceptive composition administered may be in the range of from 0.1 to 10 g, preferably 0.5 to 8 g, most preferably 1 to 5 g.

In a preferred embodiment, the contraceptive composition used in the method described above may also exhibit antimicrobial activity as described above.

Further features of the present invention will be apparent from the following Examples which are included by way of illustration, not limitation of the invention.

EXAMPLES

Example 1

Preparation of Contraceptive Composition (3% w/w Active)

TABLE 1

| Ingredients for 3% w/w contraceptive composition | | |
|---|---|---|
| Ingredient | Monograph | Quantity per batch (kg) |
| Excipients | | |
| Sodium Hydroxide NF | NF | 0.1443 |
| EDTA Disodium Dihydrate USP | USP | 0.010 |
| Methylparaben NF | NF | 0.018 |
| Propylparaben NF | NF | 0.002 |
| Carbopol ® 971P NF | NF | 0.500 |
| Propylene Glycol USP | USP | 0.100 |
| Glycerin USP | USP | 0.100 |
| Purified Water I | USP | 1.804 |
| Purified Water II | USP | 8.370 |
| Active Pharmaceutical Ingredients | | |
| SPL7013 | | 0.339 |

Protocol i. The equipment is sanitised and rinsed prior to manufacture.

ii. In a stainless steel jug, Sodium Hydroxide, NF, is dissolved in purified water.

iii. In a stainless steel vessel, EDTA Disodium Dihydrate, USP, is added to purified water and stirred with a high shear mixer until dissolved.

iv. Methyl- and Propyl-paraben, NF, are added one at a time and mixed until fully dispersed.

v. Carbopol® 971P, NF, is added slowly and the mixture stirred until the Carbopol® 971P, NF, is fully dispersed and a smooth gel is formed.

vi. Propylene glycol, USP, and Glycerin, USP, are added to the vessel and the solution mixed until the contents are fully dispersed.

vii. Sodium Hydroxide solution from Step ii. is added until the pH is greater than 4.0.

viii. SPL7013 is added in appropriate quantity calculated to give a 3% w/w gel.

ix. Sodium Hydroxide solution from Step ii. is added until the desired pH is reached, e.g. pH 4.5 or 5.0.

x. Following pH measurement, purified water is added to volume and the solution mixed until all ingredients are dispersed and a homogeneous gel is formed.

xi. The bulk yield is measured.

Example 2

Spermicidal Activity Testing

A modified Sander-Cramer Assay was conducted to assess the spermicidal activity of the contraceptive composition of the present invention. This assay determines the sperm-immobilising minimum effective concentration (MEC).

Serial two-fold dilutions were prepared from stock solutions at 2% (for water soluble compounds) or 4% (for water insoluble compounds). 250 μL of each dilution were mixed with 50 mL of a normal semen sample containing $60 \times 10^6$ motile sperm/mL. Normality of the semen samples was assessed with the aid of a CASA system (Hamilton-Thorne, IVOS; Beverly, Mass.). Semen and compound aliquots were microscopically examined while incubating at room temperature for 30 seconds. If any motile spermatozoon were found, either in the initial examination or after one hour incubation in medium, that dilution was labelled as "failed". The MEC for a given compound was calculated using the highest dilution that induces total sperm immobilization. 6 to 10 semen samples were used to obtain more reliable results. N9 (MEC=~0.1-0.2 mg/mL) and solvents were run as control. Compounds displaying MECs less than 1 mg/mL possess potent sperm-immobilising activity.

Results and Conclusion

The composition of the present invention was labelled "failed" and a MEC was not established.

It appears that the contraceptive activity of the composition of the present invention is not as a result of spermicidal activity. The spermicidal activity of the control agent N9 is due to the cytotoxic properties of this agent. Therefore, the spermicidal inactivity of the contraceptive composition suggests that it is different to N9 and that it will not be cytotoxic in humans.

Example 3

Contraceptive Effectiveness in Rabbits

The typical ejaculate of the New Zealand White rabbit contains about $2\text{-}3 \times 10^8$ sperm, which, if delivered by a cannula to the cervicovagina, delivers about 5000 Fertilizing Doses$_{50}$ (FD$_{50}$). One fertilizing doses$_{50}$, as used herein, is defined to be the quantity of sperm that will lead to 50% of a given population of rabbits becoming pregnant. In contrast, the human ejaculate delivers less than 1 FD$_{50}$. Hence, to be more relevant for predicting contraceptive efficacy in humans, both the test agent and sperm should be delivered to the cervico-vagina, and the total number of sperm delivered should be reduced.

The rabbit protocol was used to test a number of formulations, including a hydroxylcellulose (HEC) placebo gel. The test subjects were divided as shown in Table 2.

TABLE 2

Number of rabbits involved in the study

| Test material | Number of rabbits |
|---|---|
| Hydroxyethylcellulose (HEC) - (inactive control composition) | 11 |
| Active in HEC | 8 |
| Active in formulation according to Example 1 | 8 |

Female New Zealand rabbits (~7 lbs=~3 kg) were prepared by injecting 100 IU human chorionic gonadotropin (0.1 ml; Sigma) subcutaneously using a 30-gauge needle on a 1 ml syringe. The test formulation (2 ml) was deposited in the cervico-vagina of the rabbits using a flexible cannula of Tygon tubing attached to a 5 ml syringe. Fresh rabbit sperm collected from 2 male rabbits was pooled and diluted 5-fold with rabbit seminal plasma. Five minutes following test formulation administration, 0.5 ml of diluted semen (0.1 ml of semen diluted with 0.4 ml seminal plasma) was deposited in the same region at the cervico-vagina as the test formulation. This inseminating dose delivered ~10 FD$_{50}$ which is sufficient to produce an average of 7 embryos per rabbit.

Contraceptive efficacy was determined by sacrificing the animals 15 days post insemination, dissecting out the uterine horns to determine whether or not the animal became pregnant, and for the pregnant animals, counting the number of implanted embryos.

Results

TABLE 3

Results of contraceptive effectiveness study

| Test material | Number of rabbits pregnant | P value with respect to HEC placebo gel control group* | Total number of embryos across all rabbits | P value with respect to HEC placebo gel control group^ |
|---|---|---|---|---|
| HEC | 9 out of 11 | Ref value | 79 embryos | Ref value |
| Active in HEC | 2 out of 8 | 0.024 | 2 embryos | 0.005 |
| Active in formulation according to Example 1 | 2 out of 8 | 0.024 | 13 embryos | 0.03 |

*Fisher's exact, 2-tailed
^Mann-Whitney unpaired, 2-tailed

Therefore, the active in HEC or the formulation of Example 1 demonstrated significant contraceptive effects in the rabbit model when compared to the HEC placebo gel. The comparative contraceptive effects of the active in HEC or the formulation of Example 1 did not differ significantly.

After completing the above tests, pilot observations were made to estimate the duration of contraceptive efficacy and the results are summarized in the following table:

TABLE 4

Duration of contraceptive efficacy

| Time at which inseminating dose was delivered after applying test agent | HEC control animals (5 of 5 pregnant; 37 embryos) | Active in HEC | Active in Formulation according to Example 1 |
|---|---|---|---|
| 6 hours | | | 0 of 1 pregnant<br>0 embryos |
| 22-24 hours | | 0 of 1 pregnant<br>0 embryos | 0 of 1 pregnant<br>0 embryos |
| 48 hours | | | 1 of 3 pregnant<br>13 embryos |
| 7 days | | | 2 of 2 pregnant<br>16 embryos |

Combining these pilot results demonstrates that formulations with active in HEC, or according to Example 1 were highly effective contraceptives ~24 hours after application. A statistical analysis of the data in Table 4 based on an analysis of either pregnancies or number of embryos showed (i) pregnancies: P=0.05 by Fisher's exact 2-tailed test. (ii) embryos: P=0.016 via Mann-Whitney unpaired nonparametric 2-tailed test. In addition, the results at 48 hours and 7 days strongly suggest this contraceptive effect is reversible.

Conclusion

The composition of the present invention, formulated in either HEC or according to Example 1, demonstrates significant contraceptive effects in the rabbit model when delivered 5 minutes prior to artificial insemination (Table 3) and also when delivered ~24 hours prior to insemination (Table 4).

Example 4

Study to Assess the Effect of the Contraceptive Composition According to the Present Invention on HSV-2 Susceptibility The study was conducted to detect potential adverse effects of the contraceptive composition according to the present invention by measuring susceptibility of mice to infection with herpes simplex virus type 2 (HSV-2), the virus that most commonly causes genital herpes. This was important as spermicidal compositions, such as N9, had been suggested to compromise the natural vaginal barrier and significantly increase susceptibility to infection from STIs in general.

The mouse HSV-2 vaginal transmission model is used by Richard Cone at Johns Hopkins University, Baltimore, USA, to assess toxicities associated with spermicides and other contraceptive compositions that could lead to susceptibility to pathogens such as HSV-2.

Methods

Mouse Model:

Prior to the susceptibility assessment, female CF-1 mice (Harlan, Indianapolis, Ind., USA) 6-8 weeks old are progestin treated (Depo Provera®, medroxyprogesterone acetate) to increase HSV-2 susceptibility, and to make the mice more uniform in terms of susceptibility than mice at different stages of the oestrous cycle.

Viral Inoculum:

Strain G of HSV-2, $5 \times 10^8$ $TCID_{50}$/mL.

Procedures:

20 µL of a contraceptive composition according to the present invention was administered to the vagina followed 12 hours later by administration of a low-dose inoculum of HSV-2 (0.1 $ID_{50}$) delivered in 10 µL of Bartels medium. Control animals received 20 µL of PBS instead of test product.

The inoculum was delivered 12 hours after application of the test product because previous experiments (Reference: Cone R A, Hoen T E, Wang X X & Moench T R. Microbicidal Detergents Increase HSV Susceptibility in Mice Without Causing Visible Epithelial Defects. Abstract # 02421, "Microbicides 2004" Conference, London, UK; March 2004) showed that this was the time at which peak susceptibility to HSV-2 infection occurred following administration of N9.

In this study, a total of 40 mice received a contraceptive composition according to the present invention and a total of 40 mice received PBS.

Results

Only 1 out of the 40 mice treated with a contraceptive composition according to the present invention became infected with HSV-2. In contrast, 7 out of 40 mice in the control group became infected. In other words, there was no increase in susceptibility following administration of the contraceptive composition according to the present invention.

In previous studies, 29 out of 42 animals treated with N9, 20 out of 30 animals treated with spermicidal ingredient 1, and 25 out of 41 animals treated with spermicidal ingredient 2, became infected.

To determine relative susceptibility of the mice in previous studies, two groups of control mice were treated with PBS for every group of mice treated with test product. One control group was inoculated with 0.1 $ID_{50}$, while the other was inoculated with 10 $ID_{50}$. The fraction of animals infected in each control group was then used to construct a dose-response graph (fraction infected vs. log ID), drawing a linear interpolation between the low and high dose points. The fraction of mice infected in the test group was then plotted on this graph to determine the effective ID of the low-dose inoculum in this test group. Relative susceptibility was defined as the effective ID the low-dose inoculum delivered to the test mice divided by the ID it delivered to the control animals.

Animals treated with N9 were 29.7 times more susceptible to HSV-2 infection than the control animals (P<0.001, Fishers exact two-sided t-test), while animals treated with spermicidal ingredients 1 and 2 were 29.1 (P<0.001) and 17.5 (P<0.001) times more susceptible, respectively.

Conclusion

The contraceptive composition according to the present invention does not appear to lead to increased susceptibility in the mouse-model of HSV-2 infection. This study indicates that the contraceptive composition is non-cytotoxic and suggests that it will be safe for use in humans. N9 and other spermicidal microbicides may lead to increased susceptibility. (Reference: Cone R A, Hoen T E, Wang X X & Moench T R. Microbicidal Detergents Increase HSV Susceptibility in Mice Without Causing Visible Epithelial Defects. Abstract # 02421, "Microbicides 2004" Conference, London, UK; March 2004).

Example 5

Condom Compatability Study of 3% w/w of Active in Carbopol® Gel

Certain ingredients in vaginal formulations may compromise condom integrity. This method was used to determine the effect of the composition of the present invention on condoms.

Individually packaged male condoms made from natural rubber latex and intended for single use meet with certain minimum requirements specified in ASTM Designation: D 3492-97 (American Society for Testing and Materials, Standard Specification for Rubber Contraceptives, Male Condoms) test method. The test method is designed to ensure that condoms are of consistent quality. The following parameters were determined for the treated and untreated condoms: pressure at burst, volume at burst, length, thickness, and width. If the composition compromises the condoms, the pressure and volume at burst are expected to be lower. The length of the condoms might be affected as well.

For all tests, condoms were removed from their individual packages and unrolled. Using a soft brush, the entire length of each condom was coated with a gel formulation of the composition of the present invention. Individual condoms were laid on a lined tray, and incubated at 37° C. and 90% relative humidity for not less than one hour. Following each incubation period, and prior to testing, excess gel was removed from the condoms using a dry, non-abrasive cloth. Each treated condom was tested in sequential order for airburst pressure and volume. For comparison, baseline data was obtained by performing analogous testing on untreated condoms and condoms treated with placebo gel lacking any active pharmaceutical ingredients.

Data for these experiments are provided in Table 5.

TABLE 5

Airburst pressures and volumes of latex condoms following exposure to the contraceptive composition for not less than one hour.

| Condom Type | Condom Lot | Baseline | Placebo | SPL7013 Treated | Base-Placebo | Base-Treated | Placebo-Treated |
|---|---|---|---|---|---|---|---|
| | | Mean burst volume, L (n = 80) | | | Observed Change | | |
| Latex, non-lubricated | 1 | 42.8 (2.4) | 43.7 (2.7) | 45.4 (2.6) | 0.9 (0.3) | 2.6 (0.2) | 1.7 (−0.1) |
| | 2 | 44.0 (2.6) | 44.6 (2.2) | 45.6 (3.5) | 0.6 (−0.4) | 1.6 (0.9) | 1.0 (1.3) |
| | 3 | 43.9 (2.1) | 44.0 (2.5) | 44.7 (5.4) | 0.1 (0.4) | 0.8 (3.3) | 0.7 (2.9) |
| Latex, silicone-lubricated | 1 | 40.7 (3.1) | 42.5 (3.5) | 42.6 (4.0) | 1.8 (0.4) | 1.9 (0.9) | 0.1 (0.5) |
| | 2 | 42.0 (3.2) | 42.2 (3.3) | 44.1 (2.6) | 0.2 (0.1) | 2.1 (−0.6) | 1.9 (−0.7) |
| | 3 | 42.1 (3.7) | 44.5 (3.1) | 43.9 (3.0) | 2.4 (−0.6) | 1.8 (−0.7) | −0.6 (−0.1) |
| Latex, aqueous-based lubricant | 1 | 43.4 (2.8) | 42.3 (4.2) | 43.5 (4.2) | −1.1 (1.4) | 0.1 (1.4) | 1.2 (0.0) |
| | 2 | 45.3 (2.7) | 44.6 (3.7) | 45.1 (4.0) | −0.7 (1.0) | −0.2 (1.3) | 0.5 (0.3) |
| | 3 | 44.1 (3.1) | 42.5 (2.8) | 44.5 (4.2) | −1.6 (−0.3) | 0.4 (1.1) | 2.0 (1.4) |
| | | Mean Burst Pressure, kPa (n = 80) | | | Observed Change | | |
| Latex, non-lubricated | 1 | 2.0 (0.1) | 1.9 (0.1) | 1.9 (0.1) | −0.1 (0.0) | −0.1 (0.0) | 0.0 (0.0) |
| | 2 | 2.1 (0.1) | 2.0 (0.1) | 2.0 (0.1) | −0.1 (0.0) | −0.1 (0.0) | 0.0 (0.0) |
| | 3 | 2.0 (0.1) | 1.9 (0.1) | 1.9 (0.1) | −0.1 (0.0) | −0.1 (0.0) | 0.0 (0.0) |
| Latex, silicone-lubricated | 1 | 1.6 (0.1) | 1.6 (0.1) | 1.6 (0.1) | 0.0 (0.0) | 0.0 (0.0) | 0.0 (0.0) |
| | 2 | 1.7 (0.1) | 1.6 (0.1) | 1.7 (0.1) | −0.1 (0.0) | 0.0 (0.0) | 0.1 (0.0) |
| | 3 | 1.6 (0.1) | 1.5 (0.1) | 1.5 (0.1) | −0.1 (0.0) | −0.1 (0.0) | 0.0 (0.0) |
| Latex, aqueous-based lubricant | 1 | 2.1 (0.1) | 2.1 (0.2) | 2.0 (0.2) | 0.0 (0.1) | −0.1 (0.1) | −0.1 (0.0) |
| | 2 | 2.2 (0.1) | 2.2 (0.1) | 2.2 (0.2) | 0.0 (0.0) | 0.0 (0.1) | 0.0 (0.1) |
| | 3 | 2.1 (0.1) | 2.1 (0.1) | 2.1 (0.2) | 0.0 (0.0) | 0.0 (0.1) | 0.0 (0.1) |

In addition to testing the airburst pressure and volume, the tensile strength of condoms following treatment with a gel formulation of the composition of the present invention was investigated. For these tests, condoms were removed from their individual packages and unrolled. Test pieces of the condom material were cut out of the condom in accordance with ISO 4074:2002 and these pieces placed on a lined tray. The cut out test pieces of condom were all coated test pieces with the gel, placed on a lined tray and incubates at 37° C. and 90% relative humidity for not less than one hour. Following the incubation period, and prior to testing, excess lubricant was removed from sample pieces with isopropyl alcohol and the test pieces allowed to completely dry. The tensile strength of test pieces was determined in accordance with the procedure specified in ISO 4074:2002.

Data from these assays is provided in Table 6.

TABLE 6

Tensile strength and elongation properties of condom latex text pieces following exposure to the contraceptive composition for not less than one hour.

| Condom Type | Condom Lot | Baseline | Placebo | SPL7013 Treated | Base-Placebo | Base-Treated | Placebo-Treated |
|---|---|---|---|---|---|---|---|
| | | Tensile strength, N | | | Observed Change | | |
| Latex, non-lubricated | 1 | 83 | 79 | 78 | −4 | −5 | −1 |
| | 2 | 84 | 81 | 79 | −3 | −5 | −2 |
| | 3 | 85 | 83 | 80 | −2 | −5 | −3 |
| Latex, silicone-lubricated | 1 | 49 | 49 | 45 | 0 | −4 | −4 |
| | 2 | 52 | 50 | 47 | −2 | −5 | −3 |
| | 3 | 59 | 45 | 49 | −14 | −10 | +4 |
| Latex, aqueous-based lubricant | 1 | 92 | 87 | 89 | −5 | −3 | +2 |
| | 2 | 97 | 86 | 90 | −11 | −7 | +4 |
| | 3 | 83 | 79 | 83 | −4 | 0 | +4 |
| | | % Elongation | | | Observed Change | | |
| Latex, non-lubricated | 1 | 898 | 841 | 845 | −57 | −53 | +4 |
| | 2 | 891 | 834 | 837 | −57 | −54 | +3 |
| | 3 | 896 | 847 | 846 | −49 | −50 | −1 |
| Latex, silicone-lubricated | 1 | 814 | 813 | 798 | −1 | −16 | −15 |
| | 2 | 801 | 807 | 794 | +6 | −7 | −13 |
| | 3 | 831 | 795 | 808 | −36 | −23 | +13 |
| Latex, aqueous-based lubricant | 1 | 825 | 828 | 837 | +3 | +12 | +9 |
| | 2 | 833 | 821 | 836 | −12 | +3 | +15 |
| | 3 | 807 | 803 | 815 | −4 | +8 | +12 |

Results

Integrity of condoms on which the contraceptive compositions and a placebo composition were spread, as measured by air burst properties and tensile strength, was not compromised by the contraceptive compositions.

It will be appreciated that variations and modifications may be made to the invention as broadly described herein, other than those specifically described without departing from the spirit and scope of the invention. It is to be understood that this invention extends to include all such variations and modifications. It will also be understood that the invention disclosed and defined in this specification extends to all alternative combinations of two or more of the individual features mentioned or evident from the text or drawings. All of these different combinations constitute various alternative aspects of the invention.

What is claimed is:

1. A method of selectively reducing or preventing conception in a female animal, including a human, which method includes administering to the animal an effective amount of a contraceptive composition which composition includes an effective amount of a dendrimer compound including a polylysine, polyamidoamine (PAMAM), poly(etherhydroxylamine) (PEHAM) or polypropyleneimine dendrimer scaffold and one or more naphthyl disulphonic acid surface groups, or a pharmaceutically acceptable salt of the dendrimer compound; and a pharmaceutically acceptable carrier, excipient and/or diluent therefor.

2. A method according to claim 1, wherein the dendrimer compound is a compound of Formula I

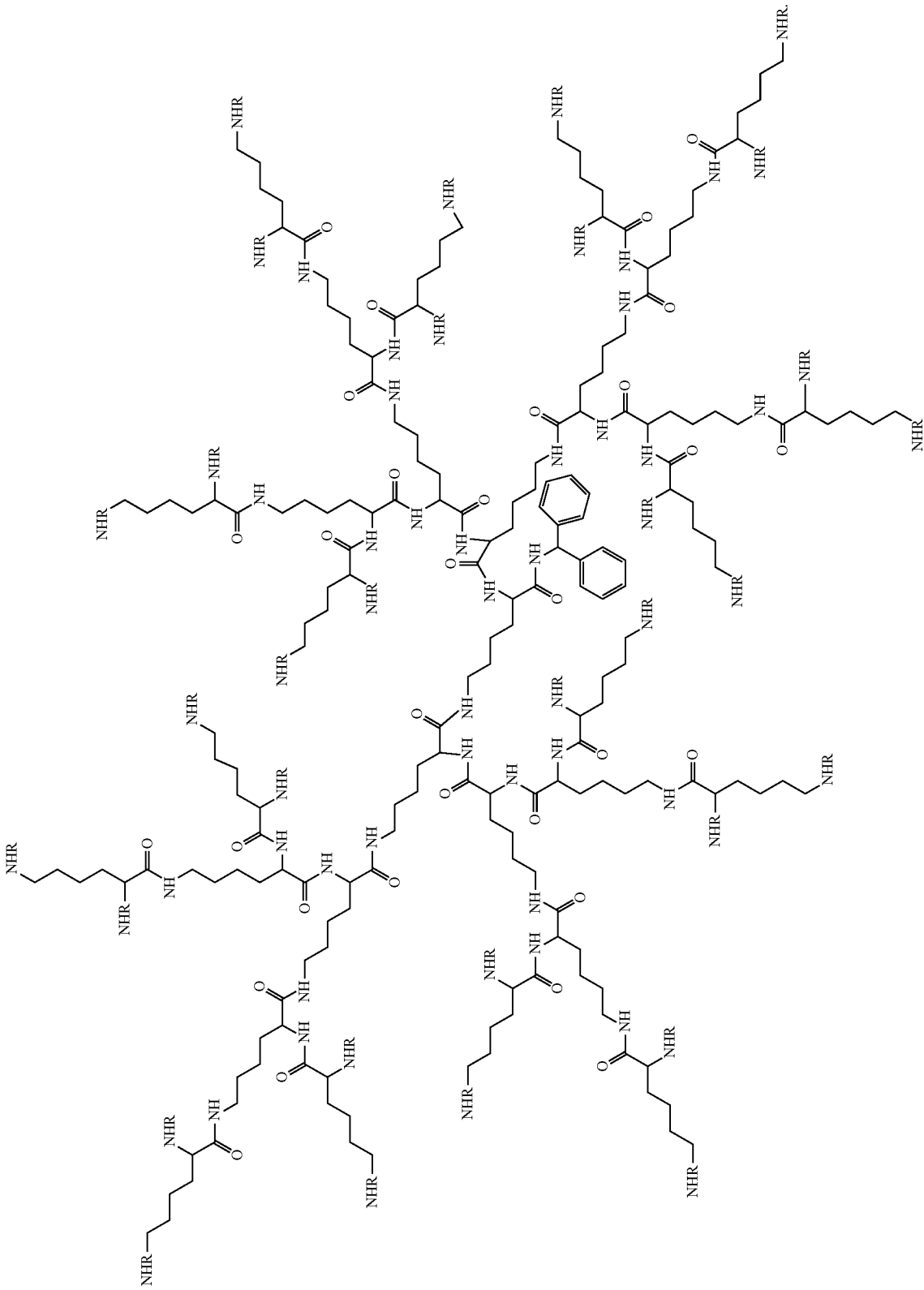

where R represents a group of Formula IV:

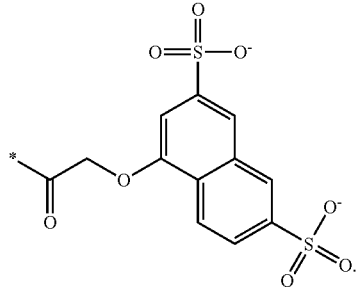

3. A method according to claim 1, wherein the contraceptive composition further includes a secondary pharmaceutically active component.

4. A method according to claim 3 wherein the secondary pharmaceutically active compound is selected from one or more of the group consisting of podophyllin, tetracycline, nystatin, fluconazole, metronidazole, acyclovir, penicillin, cefotaxime, specinomycin, retrovir, erythromycin, ceftriaxone, cotrimoxazole, cotrimoxazole, benzyl benzoate, malathion, menfegol, progestin, estrogen, and estradiol.

5. A method according to claim 1, wherein the method also reduces likelihood of infection of one or more sexually transmitted infections.

6. A method according to claim 5, wherein the sexually transmitted infections are viral infections selected from the group consisting of human immunodeficiency virus (HIV), herpes simplex (HSV), hepatitis B and hepatitis C virus (HBV and HCV), human papillomavirus (HPV) and cytomegalovirus (CMV).

7. A method according to claim 1, wherein the contraceptive composition is carried on a surface of a prophylactic device and is compatible therewith.

8. A method according to claim 7, wherein the prophylactic device is a condom.

9. A method according to claim 7, wherein the contraceptive composition is carried on an external surface of the prophylactic device.

10. A method according to claim 7, wherein the contraceptive composition further includes a secondary pharmaceutically active compound.

11. A method according to claim 10 wherein the secondary pharmaceutically active compound is selected from one or more of the group consisting of podophyllin, tetracycline, nystatin, fluconazole, metronidazole, acyclovir, penicillin, cefotaxime, specinomycin, retrovir, erythromycin, ceftriaxone, cotrimoxazole, cotrimoxazole, benzyl benzoate, malathion, menfegol, progestin, estrogen, and estradiol.

12. A method according to claim 1, wherein the dendrimer compound is selected from the group consisting of a compound of Formula II and III:

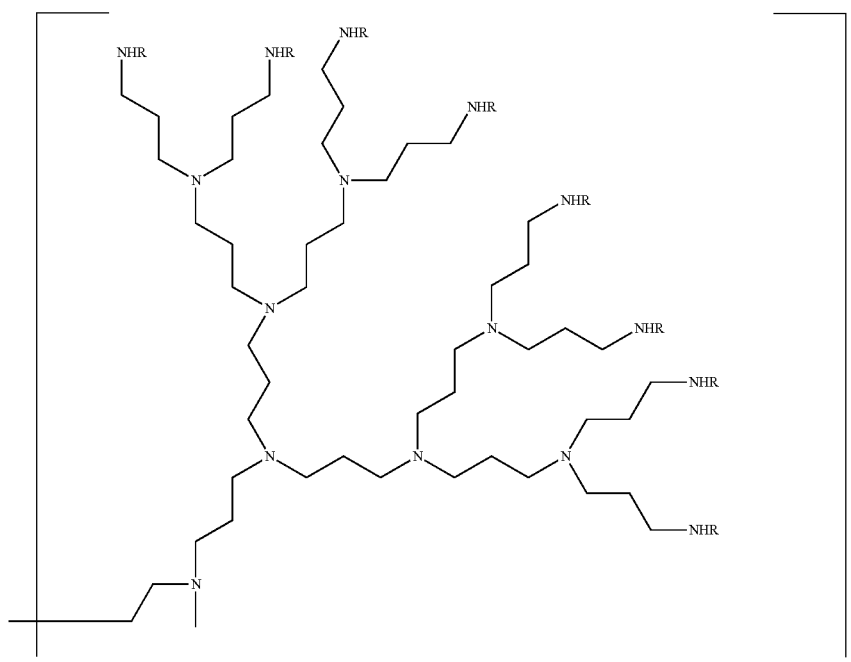

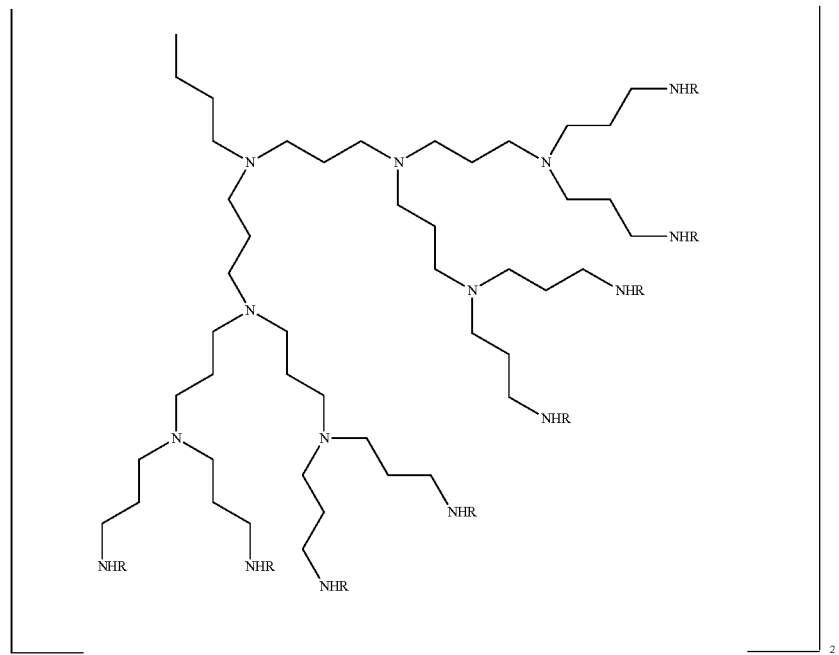
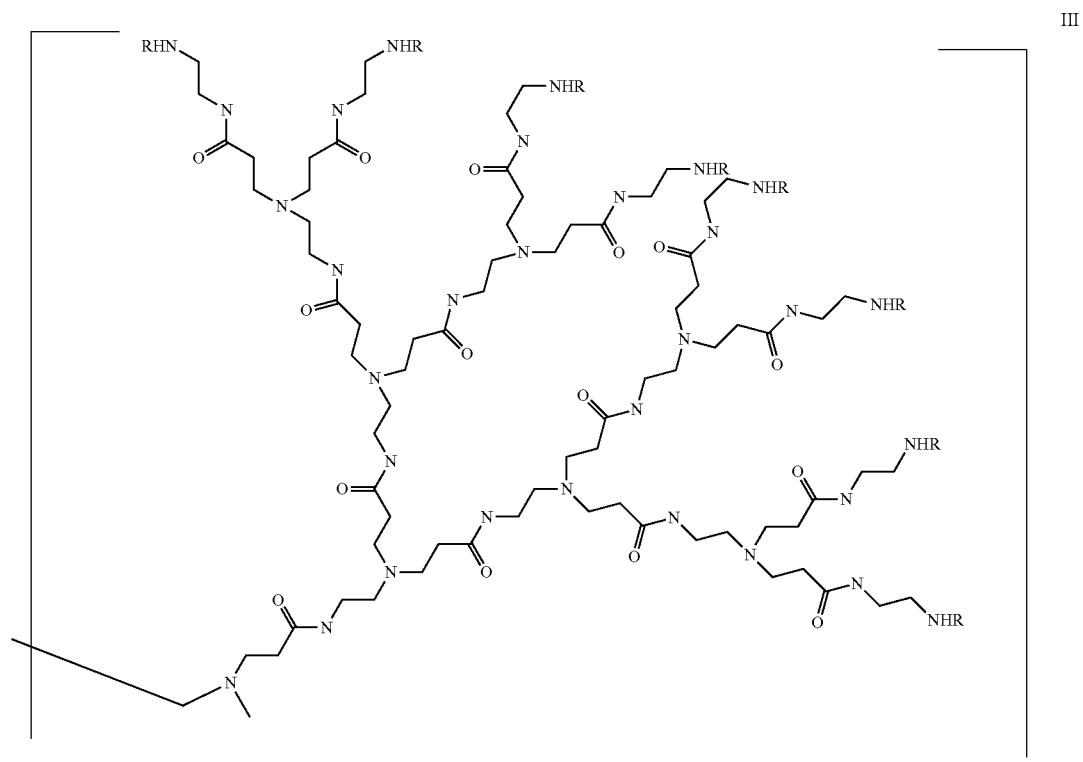

-continued

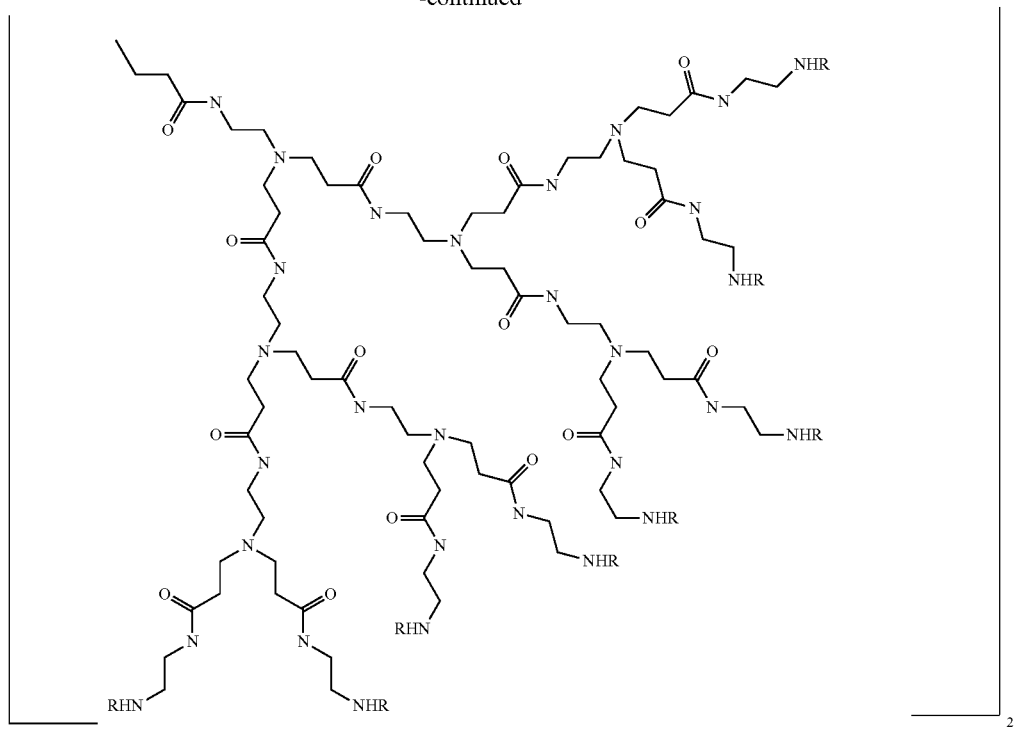

where R represents a group of Formula IV:

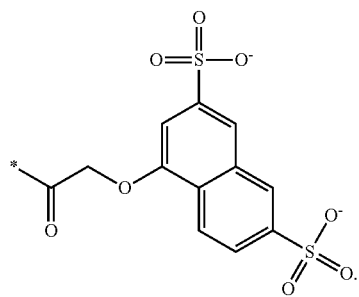

IV or a pharmaceutically acceptable salt thereof.

13. A method according to claim 1, wherein the dendrimer compound is a pharmaceutically acceptable salt of the dendrimer compound.

14. A method according to claim 13, wherein the salt is a metallic salt selected from the group consisting of one or more of aluminium, calcium, lithium, magnesium, potassium, sodium and zinc salts.

15. A method according to claim 13, wherein the salt is an organic salt selected from the group consisting of one or more of N,N'-dibenzylethylenediamine, chloroprocaine, diethanolamine, ethylenediamine, cyclohexylamine, meglumine (N-methylglucamine) and procaine.

16. A method according to claim 13, wherein the salt is selected from one or more of the group consisting of a quaternary amine, a sulphonium salt and a phosphonium salt.

17. A method according to claim 1 wherein the dendrimer compound is present in the composition in an amount of from approximately 0.5% to approximately 70% by weight, based on the total weight of the composition.

* * * * *